United States Patent
Yuan et al.

(10) Patent No.: US 12,121,601 B2
(45) Date of Patent: Oct. 22, 2024

(54) USE OF MAGNESIUM HYDRIDE IN PREPARATION OF COMPOSITION FOR PREVENTING AND TREATING CHRONIC PERIODONTITIS, AND MAGNESIUM HYDRIDE TOOTHPASTE

(71) Applicant: SHANGHAI JIAO TONG UNIVERSITY, Shanghai (CN)

(72) Inventors: Guangyin Yuan, Shanghai (CN); Wenjiang Ding, Shanghai (CN); Yueling Li, Shanghai (CN); Li Shen, Shanghai (CN); Jianxiong Yuan, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 501 days.

(21) Appl. No.: 17/614,548

(22) PCT Filed: Feb. 4, 2021

(86) PCT No.: PCT/CN2021/075140
§ 371 (c)(1),
(2) Date: Nov. 28, 2021

(87) PCT Pub. No.: WO2022/062301
PCT Pub. Date: Mar. 31, 2022

(65) Prior Publication Data
US 2022/0313570 A1      Oct. 6, 2022

(30) Foreign Application Priority Data
Sep. 23, 2020   (CN) .................. 202011011374.5

(51) Int. Cl.
| | | |
|---|---|---|
| *A61K 8/19* | (2006.01) | |
| *A61K 8/25* | (2006.01) | |
| *A61K 8/34* | (2006.01) | |
| *A61K 8/46* | (2006.01) | |
| *A61K 8/73* | (2006.01) | |
| *A61K 8/81* | (2006.01) | |
| *A61K 8/9789* | (2017.01) | |
| *A61K 33/06* | (2006.01) | |
| *A61P 1/02* | (2006.01) | |
| *A61Q 11/00* | (2006.01) | |

(52) U.S. Cl.
CPC .................. *A61K 8/19* (2013.01); *A61K 8/25* (2013.01); *A61K 8/345* (2013.01); *A61K 8/463* (2013.01); *A61K 8/73* (2013.01); *A61K 8/731* (2013.01); *A61K 8/8176* (2013.01); *A61K 8/9789* (2017.08); *A61K 33/06* (2013.01); *A61P 1/02* (2018.01); *A61Q 11/00* (2013.01); *A61K 2800/28* (2013.01); *A61K 2800/412* (2013.01); *A61K 2800/75* (2013.01)

(58) Field of Classification Search
CPC .. A61Q 11/00; A61P 1/02; A61P 29/00; A61P 31/02; A61P 31/04; A61P 39/06; A61K 8/19; A61K 8/25; A61K 8/345; A61K 8/463; A61K 8/73; A61K 8/731; A61K 8/8176; A61K 8/9789; A61K 33/06; A61K 2800/28; A61K 2800/412; A61K 2800/75; A61K 8/0241; A61K 2800/413
See application file for complete search history.

(56) References Cited

U.S. PATENT DOCUMENTS

| | | | |
|---|---|---|---|
| 6,153,219 A | 11/2000 | Creeth et al. | |
| 2010/0008849 A1 | 1/2010 | Martin | |
| 2013/0323190 A1* | 12/2013 | Ohta | A61K 33/06 424/682 |

FOREIGN PATENT DOCUMENTS

| | | |
|---|---|---|
| CN | 101951929 A | 1/2011 |
| CN | 102860971 A | 1/2013 |
| CN | 112057468 A | 12/2020 |
| WO | 2011061330 A2 | 5/2011 |
| WO | 2012061698 A2 | 5/2012 |
| WO | 2019043164 A1 | 3/2019 |
| WO | 2020023396 A1 | 1/2020 |

* cited by examiner

*Primary Examiner* — Walter E Webb
*Assistant Examiner* — Amanda Michelle Petritsch
(74) *Attorney, Agent, or Firm* — Bayramoglu Law Offices LLC

(57) ABSTRACT

The use of magnesium hydride in the preparation of a composition for preventing and treating chronic periodontitis, and a magnesium hydride toothpaste are provided. In the composition or the magnesium hydride toothpaste, magnesium hydride has a weight percentage of 1% to 3%. The toothpaste has the functions of disinfection, anti-inflammation, anti-oxidation, removing tooth stains, improving bad breath, alleviating gingival swelling, bleeding, and recession, and improving periodontitis symptoms. An appropriate amount of magnesium hydride fine particles is added in toothpaste, and the magnesium hydride particles can be hydrolyzed into hydrogen and magnesium ions with anti-inflammatory effects, which can also inhibit alveolar bone resorption. The magnesium hydride-containing composition is safe in use, and can effectively prevent the occurrence and development of periodontal diseases after long-term use.

8 Claims, No Drawings

USE OF MAGNESIUM HYDRIDE IN PREPARATION OF COMPOSITION FOR PREVENTING AND TREATING CHRONIC PERIODONTITIS, AND MAGNESIUM HYDRIDE TOOTHPASTE

CROSS REFERENCE TO THE RELATED APPLICATIONS

This application is the national phase entry of International Application No. PCT/CN2021/075140, filed on Feb. 4, 2021, which is based upon and claims priority to Chinese Patent Application No. 202011011374.5, filed on Sep. 23, 2020, the entire contents of which are incorporated herein by reference.

TECHNICAL FIELD

The present disclosure relates to the technical field of toothpaste, and in particular to the use of magnesium hydride in the preparation of a composition for preventing and treating chronic periodontitis, and a magnesium hydride toothpaste.

BACKGROUND

Brushing can help clean teeth and maintain good oral hygiene. Toothpaste is a necessity for human daily life. With the improvement of people's living standards, periodontal diseases become more prevalent due to dietary changes, neglect of oral hygiene, oral flora imbalance and the likes. In addition, the occurrence of periodontal diseases is irrelevant to age and sex.

Periodontal diseases are mainly caused by bacterial infection, and have clinical symptoms such as gingival bleeding, gingival swelling, and ulcers. Furthermore, periodontal diseases can lead to alveolar bone resorption, which may enable the teeth to loosen and fall off. In particular, periodontal diseases not only promote the spread of periodontal bacteria through the blood and lymph tissue in an affected part to involve other organs and endanger human health, but also induce mental diseases, such as depression, mania, and anxiety, through continuous neuropathic pain, thereby greatly affecting mental health.

Therefore, it is a topic for public health to effectively treat or alleviate periodontal diseases. At present, there is a need for daily tooth brushing to develop a new toothpaste with sustained and steady effects of preventing potential periodontal diseases and controlling or treating occurred periodontal diseases and small side effects.

At present, the commercially available toothpaste with the addition of peroxide mainly utilize the peroxide for disinfection to keep the oral environment healthy. However, these toothpaste have a single function and a short service life. There are also kinds of toothpaste that use traditional Chinese medicine (TCM) ingredients to achieve a disinfection effect (for example, the Chinese Patent No. CN102860971A discloses a compound toothpaste with anti-bacterial, anti-inflammatory, and desensitizing effects, where natural propolis and TCMs with analgesic, anesthetic, and anti-allergic effects are used as main functional ingredients, and are compounded with traditional western medicines to prepare the compound toothpaste by a biological technology). However, various TCM additives may cause obvious side effects, and such products cannot enter the international market due to unknown TCM composition and inexact efficacy.

These periodontal diseases are mainly caused by periodontal bacteria and lead to inflammation and alveolar bone resorption, so it is quite important for preventing or treating periodontal diseases by means of disinfection, anti-inflammation, and inhibition of alveolar bone resorption.

SUMMARY

The problem to be solved by the present disclosure is to provide use of magnesium hydride in the preparation of a composition for preventing and treating chronic periodontitis, and a magnesium hydride toothpaste. The magnesium hydride toothpaste has a new toothpaste formula. In addition to daily teeth and oral cleaning, the magnesium hydride toothpaste has the effects of disinfection, anti-inflammation, improving gingival swelling or bleeding and bad breath, removing tooth stains for whitening, etc. Moreover, the magnesium hydride toothpaste involves low cost and has the dual function of health care and treatment.

The objective of the present disclosure is achieved by the following technical solutions.

The present disclosure provides use of magnesium hydride in the preparation of a composition for preventing and treating chronic periodontitis, and in the composition, the magnesium hydride has a weight percentage of 1% to 3%.

Preferably, the magnesium hydride may have a particle size of 0.1 µm to 100 µm.

The present disclosure provides use of magnesium hydride in the preparation of toothpaste, and in the toothpaste, the magnesium hydride has a weight percentage of 1% to 3%.

Preferably, the magnesium hydride may have a particle size of 0.1 µm to 100 µm.

The present disclosure provides a magnesium hydride toothpaste, including the following components, in weight percentage:

15% to 51% of glycerin and/or paraffin oil,
0% to 30% of 1,2-propanediol,
42% to 45% of calcium carbonate,
2% to 5% of silicon dioxide,
0% to 3% of sodium dodecyl sulfate (SDS),
1% to 3% of magnesium hydride,
0% to 1% of sodium carboxymethyl cellulose (CMC-Na),
0% to 0.3% of xanthan gum,
0% to 3% of polyvinylpyrrolidone (PVP), and
0% to 1% of peppermint powder.

Preferably, the toothpaste may include the following components, in weight percentage: 51% of the glycerin, 42% of the calcium carbonate, 2% of the silicon dioxide, 3% of the SDS, 1% of the magnesium hydride, and 1% of the peppermint powder.

Preferably, the toothpaste may include the following components, in weight percentage: 33.4% of the paraffin oil, 14.3% the glycerin, 43% of the calcium carbonate, 2% of the silicon dioxide, 3% of the SDS, 1% of the CMC-Na, 0.3% of the xanthan gum, 2% of the magnesium hydride, and 1% of the peppermint powder.

Preferably, the toothpaste may include the following components, in weight percentage: 29% of the 1,2-propanediol, 15% of the glycerin, 44% of the calcium carbonate, 5% of the silicon dioxide, 3% of the PVP, 3% of the magnesium hydride, and 1% of the peppermint powder.

Preferably, the magnesium hydride may have a particle size of 0.1 µm to 100 µm.

The magnesium hydride of the present disclosure can react with water to generate magnesium hydroxide and hydrogen, and the magnesium hydroxide can be degraded into magnesium ions in an acidic oral environment, which also promotes the oral environment to be neutral or weakly alkaline. As small molecules, hydrogen molecules can freely penetrate tissues and cells to reach any location.

As hydrogen and magnesium ions have the effects of disinfection, anti-oxidation, anti-inflammation, and inhibition of alveolar bone resorption, the magnesium hydride-containing toothpaste of the present disclosure can achieve effective whitening, disinfection, and anti-inflammation effects, and can also effectively prevent the occurrence and development of periodontal diseases.

Compared with the prior art, the present disclosure has the following beneficial effects.

1. The present disclosure provides a new toothpaste (magnesium hydride toothpaste) that can release hydrogen and magnesium ions during tooth brushing. In the present disclosure, some of the toothpaste is taken and placed in water, and then a hydrogen concentration and a magnesium ion concentration in the water are detected, which proves that the magnesium hydride toothpaste can significantly release hydrogen and magnesium ions; a bactericidal activity test is conducted, which proves that the magnesium hydride toothpaste can effectively kill bacteria; and small-scale clinical trials are conducted, which proves that the magnesium hydride toothpaste can prevent and treat chronic periodontitis.

2. The present disclosure found that the magnesium hydride toothpaste can alleviate periodontal diseases: 50 patients with chronic periodontitis were selected according to inclusion criteria: well overall health status, no important systemic diseases, and age: 18 to 60 years old; and exclusion criteria: open dental caries or mucosal lesions in the oral cavity, and severe periodontitis. The patients continuously used the magnesium hydride toothpaste of the present disclosure for 30 d according to the following usage: brushing frequency: 2 times/day; toothpaste dosage: 2 g/time; and brushing time: 3 min/time. (Organization unit: Dental Clinic of Jiading District, Shanghai. The experiment was approved by the Ethics Committee.) Through this experiment, it is found that the magnesium hydride toothpaste has the effects of improving gingival bleeding, gingival swelling, and bad breath, removing tooth stains, etc. (In the present disclosure, 5 groups of patients with chronic periodontitis (corresponding to five kinds of toothpaste with 0 wt % $MgH_2$ (except that no $MgH_2$ is included, the remaining components are the same as in Example 1), 0.5 wt % $MgH_2$, 1 wt % $MgH_2$, 2 wt % $MgH_2$, and 3 wt % $MgH_2$, respectively) were selected, with 50 patients in each group, and a total of 250 patients participated in related clinical trials. Details can be seen in Effectiveness Verification II: Research on Treatment of Magnesium Hydride Toothpaste for Patients with Chronic Periodontitis).

3. The magnesium hydride toothpaste of the present disclosure can be prepared by a simple method with low cost, has no toxic and side effects, and can well diminish inflammation, improve gingival bleeding, gingival swelling, and bad breath, remove tooth stains, etc., thereby preventing and alleviating clinical symptoms caused by periodontal diseases.

DETAILED DESCRIPTION OF THE EMBODIMENTS

The present disclosure is described in detail below with reference to specific examples. The following examples will help those skilled in the art to further understand the present disclosure, but do not limit the present disclosure in any way. It should be noted that those of ordinary skill in the art can further make several variations and improvements without departing from the idea of the present disclosure. These all fall within the protection scope of the present disclosure.

It should be noted that, in examples, when a particle size of magnesium hydride is in the range of 0.1 μm to 100 μm, a prepared magnesium hydride toothpaste can have similar effects to the following examples.

Example 1: Toothpaste was prepared from the following components in weight percentage: glycerin: 51%, calcium carbonate: 42%, silicon dioxide: 2%, SDS: 3%, magnesium hydride (with a particle size of 10 μm to 30 μm): 1%, and peppermint powder: 1%.

The toothpaste was prepared as follows:

The magnesium hydride was composed of $MgH_2$ compound particles with a particle size of 0.1 μm to 100 μm. The toothpaste can be prepared by a traditional toothpaste preparation process. Specifically, the magnesium hydride toothpaste in this example was prepared as follows: the above components were weighed, and dispersed and mixed in a pre-dispersion kettle to obtain a liquid material, and a vacuum pump of a paste preparation kettle was turned on to pump the liquid material into the paste preparation kettle; then a scraper, a stirrer, and a colloid mill were turned on; 50 min later, the colloid mill, the stirrer, and the scraper were turned off sequentially, and vacuum breaking was conducted to obtain the magnesium hydride toothpaste; and samples were collected for test.

Example 2: Toothpaste was prepared from the following components in weight percentage: paraffin oil: 33.4%, glycerin: 14.3%, calcium carbonate: 43%, silicon dioxide: 2%, SDS: 3%, CMC-Na: 1%, xanthan gum: 0.3%, magnesium hydride (with a particle size of 10 μm to 30 μm): 2%, and peppermint powder: 1%.

The magnesium hydride toothpaste in Example 2 was prepared according to the preparation method in Example 1.

Example 3: Toothpaste was prepared from the following components in weight percentage: 1,2-propanediol: 29%, glycerin: 15%, calcium carbonate: 44%, silicon dioxide: 5%, PVP: 3%, magnesium hydride (with a particle size of 10 μm to 30 μm): 3%, and peppermint powder: 1%.

The magnesium hydride toothpaste in Example 3 was prepared according to the preparation method in Example 1.

As magnesium hydride is added, the toothpaste of the present disclosure has the effects of anti-oxidation, removing tooth stains and whitening, and effectively inhibiting inflammation, shows high stability, and can effectively prevent and alleviate a series of clinical symptoms caused by periodontitis.

Comparative Example 1: Toothpaste was prepared from the following components in weight percentage: glycerin: 51%, calcium carbonate: 43%, silicon dioxide: 2%, SDS: 3%, and peppermint powder: 1%.

The toothpaste was prepared by the same process as in Example 1.

Comparative Example 2: Toothpaste was prepared from the following components in weight percentage: glycerin: 51%, calcium carbonate: 42.5%, silicon dioxide: 2%, SDS: 3%, magnesium hydride (with a particle size of 10 μm to 30 μm): 0.5%, and peppermint powder: 1%. The toothpaste was prepared by the same process as in Example 1.

Effectiveness Verification:

I. Determination of Concentrations of Hydrogen and Magnesium Ions Released from the Magnesium Hydride Toothpaste 1. Experimental Method 1.1 Materials: the magnesium hydride toothpaste of Examples 1 to 3 (several toothbrushes, hydrogen measuring instrument, ultrasonic instrument, water, several small glass cups (15 ml in volume), ICP-AES analyzer (atomic emission spectrometer, USA).

1.2 Experimental steps:

1) The magnesium hydride toothpaste was applied to a toothbrush.

2) The toothbrush was placed in a small glass cup with 5 ml of water to apply the toothpaste on a glass wall.

3) The small glass cup was placed in the ultrasonic instrument for 1 min to promote the dissolution of the toothpaste, then taken out, and stood at room temperature.

4) The hydrogen measuring instrument was used to detect hydrogen concentrations when the small glass cup stood for 1 min and 3 min.

5) ICP-AES was used to detect a magnesium ion concentration.

6) Five replicates were set for each example, and results were expressed as mean±standard deviation (SD).

2. Test results of hydrogen and magnesium ion concentrations were shown in Table 1.

TABLE 1

| Sample | Hydrogen concentration at 1 min (ppb) | Hydrogen concentration at 3 min (ppb) | Magnesium ion concentration (ppm) |
|---|---|---|---|
| Magnesium hydride toothpaste of Example 1 | 900 | 1100 | 5.0 |
| Magnesium hydride toothpaste of Example 2 | 950 | 1200 | 7.7 |
| Magnesium hydride toothpaste of Example 3 | 990 | 1400 | 10.0 |

3. Conclusion: The magnesium hydride toothpaste can produce high concentrations of hydrogen and magnesium ions.

II. Research on Treatment of Magnesium Hydride Toothpaste for Patients with Chronic Periodontitis (1) Clinical Utility of Example 1:

50 subjects were recruited.

Toothpaste formula used: the formula described in Example 1 (glycerin+magnesium hydride).

Inclusion criteria: well overall health status, no important systemic diseases, and age: 18 to 60 years old.

Exclusion criteria: open dental caries or mucosal lesions in the oral cavity, and severe periodontitis.

Usage: brushing frequency: 2 times/day; toothpaste dosage: 2 g/time; and brushing time: 3 min/time. The toothpaste was continuously used for 30 d.

Organization unit: Dental Clinic of Jiading District, Shanghai. The experiment was approved by the Ethics Committee.

After the experiment, a questionnaire was conducted for the participants. The effect feedback obtained was shown in Table 2.

TABLE 2

Utility feedback of the magnesium hydride toothpaste in Example 1

| | Prominent (number of subjects) | General (number of subjects) | Almost none (number of subjects) | Completely none (number of subjects) |
|---|---|---|---|---|
| Cleaning power | 38 | 11 | 1 | 0 |
| Improvement on gingival bleeding | 19 | 18 | 10 | 3 |
| Improvement on gingival swelling | 22 | 21 | 6 | 1 |
| Improvement on bad breath | 37 | 6 | 5 | 2 |

2. Experimental Subject:

Inclusion criteria: those who are at an age of 18 to 60 and diagnosed with chronic periodontitis through clinical examination (with reference to the diagnostic criteria of chronic periodontitis proposed by American Periodontal Disease Classification Symposium in 1999), have at least 18 completely-erupted teeth in the oral cavity and 4 or more sites with a periodontal pocket depth of 6 mm to 9 mm in at least 2 quadrants of the oral cavity, and are willing to sign an informed consent form, and voluntarily and able to ensure follow-up, reexamination, and treatment in accordance with a research schedule within a specified time period.

Exclusion criteria: smokers, alcohol abusers, and drug abusers; those who have received antibiotic treatment or periodontal sequential treatment in recent 3 months; those who have uncontrolled diabetes, hypertension, and other systemic diseases that cannot tolerate periodontal sequential treatment; those with acute symptoms; those who are taking drugs that affect the periodontal condition (glucocorticoids, phenytoin, nifedipine, cyclosporine A, etc.); and those who are pregnant or breastfeeding or intended for conception during a planned treatment period.

The ethics committee approved. The patients signed an informed consent form.

Intervention and Clinical Examination

The 5 groups of patients all accepted oral hygiene education and ultrasonic supragingival scaling. One week later, the periodontal clinical indexes (baseline level) were checked, then SRP was conducted with a subgingival curette, and the periodontal pocket and root surface were checked to confirm that the root surface was fully cleaned and smoothed. The 5 groups of patients brushed their teeth with a special toothbrush (provided by the dental clinic) and a corresponding toothpaste according to a correct tooth brushing method recommended. All included patients underwent a comprehensive periodontal clinical examination 1 week (baseline), 6 weeks, and 12 weeks after the supragingival scaling. Clinical examination indexes included: probing pocket depth (PD), clinical attachment level (CAL), and bleeding on probing (BOP).

3. Conclusion: The toothpaste with 1% magnesium hydride can effectively improve gingival bleeding, gingival swelling, and bad breath.

(2) Clinical Utility of Example 2:

50 subjects were recruited.

Inclusion criteria: well overall health status, no important systemic diseases, and age: 18 to 60 years old.

Exclusion criteria: open dental caries or mucosal lesions in the oral cavity, and severe periodontitis.

Usage: brushing frequency: 2 times/day; toothpaste dosage: 2 g/time; and brushing time: 3 min/time. The toothpaste was continuously used for 30 d.

Organization unit: Dental Clinic of Jiading District, Shanghai. The experiment was approved by the Ethics Committee.

The effect feedback obtained was shown in Table 3.

TABLE 3

Utility feedback of the magnesium hydride toothpaste in Example 2

| Utility feedback of the magnesium hydride toothpaste in Example 2 | Prominent (number of subjects) | General (number of subjects) | Almost none (number of subjects) | Completely none (number of subjects) |
| --- | --- | --- | --- | --- |
| Cleaning power | 40 | 10 | 0 | 0 |
| Improvement on gingival bleeding | 21 | 20 | 8 | 2 |
| Improvement on gingival swelling | 23 | 21 | 5 | 1 |
| Improvement on bad breath | 39 | 4 | 5 | 2 |

Conclusion: The toothpaste with 2% magnesium hydride can effectively improve gingival bleeding, gingival swelling, and bad breath.

(3) Clinical Utility of Example 3

50 subjects were recruited.

Inclusion criteria: well overall health status, no important systemic diseases, and age: 18 to 60 years old.

Exclusion criteria: open dental caries or mucosal lesions in the oral cavity, and severe periodontitis.

Usage: brushing frequency: 2 times/day; toothpaste dosage: 2 g/time; and brushing time: 3 min/time. The toothpaste was continuously used for 30 d.

Organization unit: Dental Clinic of Jiading District, Shanghai. The experiment was approved by the Ethics Committee.

The effect feedback obtained was shown in Table 4.

TABLE 4

Utility feedback of the magnesium hydride toothpaste in Example 3

| | Prominent (number of subjects) | General (number of subjects) | Almost none (number of subjects) | Completely none (number of subjects) |
| --- | --- | --- | --- | --- |
| Cleaning power | 42 | 8 | 0 | 0 |
| Improvement on gingival bleeding | 22 | 19 | 8 | 1 |
| Improvement on gingival swelling | 25 | 19 | 5 | 1 |
| Improvement on bad breath | 41 | 5 | 3 | 1 |

Conclusion: The toothpaste with 2% magnesium hydride can effectively improve gingival bleeding, gingival swelling, and bad breath.

According to the utility of Examples 1, 2, and 3, the magnesium hydride contents of 1% to 3% can lead to a significant effect, and toothpaste with the magnesium hydride contents all can effectively improve gingival bleeding, gingival swelling, and bad breath. There is no significant difference in utility among the three examples with the content of 1% to 3%.

(4) Clinical Trial Effects of the Comparative Example

Utility feedback of the toothpaste of Comparative Example 1 (without $MgH_2$, corresponding to Example 1)

50 subjects were recruited.

Inclusion criteria: well overall health status, no important systemic diseases, and age: 18 to 60 years old.

Exclusion criteria: open dental caries or mucosal lesions in the oral cavity, and severe periodontitis.

Results were shown in Table 5.

TABLE 5

Utility feedback of the magnesium hydride toothpaste in Comparative Example 1

| | Prominent (number of subjects) | General (number of subjects) | Almost none (number of subjects) | Completely none (number of subjects) |
| --- | --- | --- | --- | --- |
| Cleaning power | 37 | 12 | 1 | 0 |
| Improvement on gingival bleeding | 1 | 5 | 29 | 15 |
| Improvement on gingival swelling | 1 | 3 | 31 | 15 |
| Improvement on bad breath | 0 | 5 | 27 | 18 |

Conclusion: The toothpaste without magnesium hydride (the remaining components are the same as in Example 1) shows a prominent oral cleaning effect on the subjects, but cannot significantly improve gingival bleeding, gingival swelling, and bad breath. In contrast to the utility of Example 1, it can be confirmed that the magnesium hydride in the toothpaste makes a significant contribution to improving gingival bleeding, gingival swelling, and bad breath.

III. Antibacterial test of $MgH_2$ toothpaste

1. Experimental Purpose: Testing the Bactericidal Activities of the 3 Kinds of Toothpastes with Different Magnesium Hydride Contents 2. Experimental Materials (1) Test samples: the magnesium hydride toothpaste prepared in Examples 1, 2, and 3, with magnesium hydride contents of 1%, 2%, and 3%, respectively; and the toothpaste prepared in Comparative Examples 1 and 2, with magnesium hydride contents of 0% and 0.5%, respectively (the remaining components were the same as in Example 1 to facilitate comparison with Example 1).

(2) Test strains: *Escherichia coli* (*E. coli*) ATCC 8739; *Staphylococcus aureus* (*S. aureus*) ATCC 25923; and *Candida albicans* (*C. albicans*).

(3) Media: LB medium (for the cultivation of *E. coli* and *S. aureus*); and YPD medium (for the cultivation of *C. albicans*).

3. Experimental Scheme

Single colonies were picked and inoculated into 2 mL of a liquid medium, and cultivated overnight; a bacterial concentration was adjusted with a corresponding medium to an $OD_{600}$ of about 0.5, and then diluted 100 times with the medium to obtain a bacterial suspension for later use; 1 g of toothpaste or a control substance was weighed and added into the bacterial suspension (with 2 to 3 glass beads to disperse the toothpaste), and a resulting mixture was shaken to dissolve the toothpaste, stood for 3 min, and then was serially diluted with sterile normal saline; and counting was conducted for diluted samples by spot inoculation, and a bactericidal rate was calculated.

4. Experimental Results

TABLE 6

Test results of bactericidal rate (%)

| | E. coli | S. aureus | C. albicans |
|---|---|---|---|
| 1% MgH$_2$ toothpaste (Example 1) | 60% | 100% | 100% |
| 2% MgH$_2$ toothpaste (Example 2) | 93% | 100% | 100% |
| 3% MgH$_2$ toothpaste (Example 3) | 100% | 100% | 100% |
| Toothpaste of Comparative Example 1 (with 0% MgH$_2$) | 0% | 100% | 100% |
| Toothpaste of Comparative Example 2 (with 0.5% MgH$_2$) | 28% | 100% | 100% |

It can be seen from experimental results shown in Table 6 that, compared with the toothpaste in the control group 1 (without MgH$_2$) and the control group 2 (low MgH$_2$ content (0.5%)), the toothpaste of the present disclosure show significant bactericidal effects on common *E. coli*, *S. aureus*, and *C. albicans*; and the toothpaste in the control group 1 (without MgH$_2$) and the control group 2 (low MgH$_2$ content (0.5%)) have no significant bactericidal effect on *E. coli*.

Combining the above antibacterial experiment results and the actual feedback results of the 5 groups of clinical subjects, it can be confirmed that the toothpaste with magnesium hydride (1 wt % to 3 wt %) of the present disclosure has significant antibacterial effects, and can improve gingival bleeding and gingival swelling and eliminate bad breath.

There are many ways to specifically apply the present disclosure, and the above are merely preferred implementations of the present disclosure. It should be noted that the foregoing examples are provided only for illustrating the present disclosure and are not intended to limit the protection scope of the present disclosure. For a person of ordinary skill in the art, several improvements may further be made without departing from the principle of the present disclosure, and these improvements should also be considered as falling within the protection scope of the present disclosure.

What is claimed is:

1. A magnesium hydride toothpaste, comprising
   15 wt % to 51 wt % of glycerin and/or paraffin oil,
   0 wt % to 30 wt % of 1,2-propanediol,
   42 wt % to 45 wt % of calcium carbonate,
   2 wt % to 5 wt % of silicon dioxide,
   0 wt % to 3 wt % of sodium dodecyl sulfate (SDS),
   1 wt % to 3 wt % of magnesium hydride,
   0 wt % to 1 wt % of sodium carboxymethyl cellulose (CMC-Na),
   0 wt % to 0.3 wt % of xanthan gum,
   0 wt % to 3 wt % of polyvinylpyrrolidone (PVP), and
   0 wt % to 1 wt % of peppermint powder.

2. The magnesium hydride toothpaste according to claim 1, comprising
   51 wt % of the glycerin,
   42 wt % of the calcium carbonate,
   2 wt % of the silicon dioxide,
   3 wt % of the SDS,
   1 wt % of the magnesium hydride, and
   1 wt % of the peppermint powder.

3. The magnesium hydride toothpaste according to claim 1, comprising
   33.4 wt % of the paraffin oil,
   14.3 wt % the glycerin,
   43 wt % of the calcium carbonate,
   2 wt % of the silicon dioxide,
   3 wt % of the SDS,
   1 wt % of the CMC-Na,
   0.3 wt % of the xanthan gum,
   2 wt % of the magnesium hydride, and
   1 wt % of the peppermint powder.

4. The magnesium hydride toothpaste according to claim 1, comprising
   29 wt % of the 1,2-propanediol,
   15 wt % of the glycerin,
   44 wt % of the calcium carbonate,
   5 wt % of the silicon dioxide,
   3 wt % of the PVP,
   3 wt % of the magnesium hydride, and
   1 wt % of the peppermint powder.

5. The magnesium hydride toothpaste according to claim 1, wherein the magnesium hydride has a particle size of 0.1 μm to 100 μm.

6. The magnesium hydride toothpaste according to claim 2, wherein the magnesium hydride has a particle size of 0.1 μm to 100 μm.

7. The magnesium hydride toothpaste according to claim 3, wherein the magnesium hydride has a particle size of 0.1 μm to 100 μm.

8. The magnesium hydride toothpaste according to claim 4, wherein the magnesium hydride has a particle size of 0.1 μm to 100 μm.

* * * * *